United States Patent [19]

Da Cunha et al.

[11] Patent Number: 5,356,627
[45] Date of Patent: Oct. 18, 1994

[54] WATERPROOF COSMETIC COMPOSITIONS

[75] Inventors: Kathleen Da Cunha, Stamford, Conn.; Lisa Denninger, Amityville, N.Y.; Katherine Stevens, Islip Terrace, N.Y.; Rebecca Pasciuta, North Babylon, N.Y.

[73] Assignee: Estee Lauder, Inc., New York, N.Y.

[21] Appl. No.: 12,089

[22] Filed: Feb. 1, 1993

[51] Int. Cl.$^5$ .................. A61K 7/02; A61K 7/032
[52] U.S. Cl. ..................... 424/401; 424/63; 514/937; 514/938
[58] Field of Search ............ 424/401, 63; 514/937, 514/938

[56] References Cited

U.S. PATENT DOCUMENTS

| | | | |
|---|---|---|---|
| 3,266,995 | 8/1966 | Lanzet et al. | 167/90 |
| 3,641,239 | 2/1972 | Mohrlok | 424/64 |
| 4,423,031 | 12/1983 | Murui et al. | 424/63 |
| 4,578,266 | 3/1986 | Tietjen et al. | 424/63 |
| 4,584,341 | 4/1986 | Huebner et al. | 524/837 |
| 4,855,129 | 8/1989 | Steinbach et al. | 424/63 |
| 4,988,502 | 1/1991 | Ounanian et al. | 424/63 |
| 5,053,221 | 10/1991 | Robertson et al. | 424/63 |
| 5,061,481 | 10/1991 | Suzuki et al. | 424/63 |
| 5,066,485 | 11/1991 | Brieva et al. | 424/63 |
| 5,108,736 | 4/1992 | Schlossman | 424/64 |
| 5,118,496 | 6/1992 | Herstein | 424/63 |
| 5,183,588 | 2/1993 | Salerno et al. | 514/938 |

FOREIGN PATENT DOCUMENTS 1140536 1/1969 United Kingdom .

OTHER PUBLICATIONS

Rit et al., "A New Beeswax Derivative for Cosmetic Formulations", Cosmetics & Toiletries 105:53–61 (1990).

Primary Examiner—Thurman K. Page
Assistant Examiner—Amy Hulina
Attorney, Agent, or Firm—Pennie & Edmonds

[57] ABSTRACT

The present invention relates to a novel waterproof cosmetic composition, useful as a mascara which contains a dimethicone-silica copolymer in an emulsion system.

21 Claims, No Drawings

WATERPROOF COSMETIC COMPOSITIONS

FIELD OF THE INVENTION

The present invention relates to waterproof cosmetic compositions which comprise a water based silicone elastomer in an emulsion system. In particular, the invention relates to waterproof cosmetic compositions which are useful for various applications to skin and hair, especially for applications to the eyelashes and eyebrows, i.e., mascara.

BACKGROUND OF THE INVENTION

Cosmetics are generally used to improve the physical appearance of a person, for example, to impart a healthy, youthful or stylish appearance. Cosmetics are broadly classified into basic groups, such as lotions, creams, emulsions, packs, and the like. In addition, cosmetics include foundations, lipsticks, rouges, eyeliners, mascaras, eyeshadows, eyebrow pencils, face powders and the like. These cosmetics are most commonly applied to the skin, hair and nails and usually provide coloring and sometimes softness and suppleness by moisturizing the areas to which they are applied.

Because cosmetics are applied to the skin, hair and nails, it is important that they have a good adhesion. Cosmetics, such as mascaras are utilized to enhance beauty by coating eyelashes and, in some cases, eyebrows, to make them more attractive by providing color. Mascaras should not only have good adhesion properties but also should apply evenly and remain in place without flaking, smearing, smudging or running. Cosmetics, such as mascara, should ideally be water-resistant, oil-resistant and friction-resistant while retaining a comfortable feel and brilliant coloring.

Moreover, mascaras should provide excellent build. The user should be able to layer applications of the mascara for more brilliant color without encountering lumping, etc. Water-resistance or waterproofness is particularly desirable for cosmetics such as mascara because human secretions, such as sweat, tears and the like; and moisture such as rain and snow, which the user is likely to encounter daily, can interact with the mascara and cause running or removal. In addition, the mascara user would need waterproof mascara if they want to prevent problems with swimming pool or ocean water which would otherwise react with the cosmetic and/or remove it. Similarly, friction-resistance is desirable for cosmetics, such as mascara, because of the potential for contact with hands and clothes. Although it is desirable to have a mascara which is water and friction resistant, it is also desirable to have a mascara which is easily removable by the user after use.

Those skilled in the art are well aware that most waterproof mascaras either have a heavy feel, smudge or flake easily, are difficult to remove, or have a potential for loss of eyelash or eyebrow hair. In an effort to provide a mascara which has all of the desirable benefits while having few or no undesirable disadvantages, several mascaras have been designed. Some have been designed without the use of waxes, heavy oils, heavy film formers and plasticizers. Further, mascaras have even been designed without pigments, i.e., no-color mascara compositions. It has been a challenge to those skilled in the art, to prepare a waterproof mascara which has advantages such as brilliant color, comfortable feel and which is easily removable.

For example, waterproof mascaras have been developed utilizing water based acrylic polymers. While these mascaras are waterproof and provide soap and water washability, they demonstrate poor performance, (i.e., smudging, flaking, etc. commonly occur) due to the incompatibility of the acrylic polymer with the other components of the formulation. In addition, several oil soluble film forming raw materials such as tall oil glycerides, have been used to achieve a waterproof film. These materials have resulted in a film which is extremely difficult to remove. Finally, a number of silicone polymers, which are soluble only in organic solvents, have been utilized. Cosmetics prepared from these are water-resistant but fail to provide either good build on lashes or easy removal, i.e., they are not removable with soap and water.

As mentioned above, it is desirable to develop a waterproof mascara that provides excellent build and color and yet has easy removal characteristics.

SUMMARY OF THE INVENTION

It is an object of the present invention to provide a cosmetic composition that provides a flexible, natural waterproof film with excellent build on eyelashes.

It is an object of the present invention to provide a novel waterproof cosmetic composition which is easily removable with soap and water.

Further, it is an object of the present invention to provide a quick drying cosmetic composition useful as a mascara, which is waterproof, provides brilliant color and yet does not smudge or flake.

A novel waterproof cosmetic composition useful as a mascara has been developed which provides a flexible, natural waterproof film, excellent build and easy removal while eliminating flaking, smudging and other undesirable effects. The novel waterproof composition of the present invention is an emulsion system comprising a water based silicone elastomer.

The novel waterproof cosmetic composition of the present invention comprises a dimethicone-silica copolymer in an emulsion system, such as a water-in-oil or oil-in-water emulsion. In a preferred embodiment, the waterproof cosmetic composition also utilizes volatile organic solvents, colorants and waxes; and optionally, cosmetically acceptable fillers, preservatives and emulsifiers. These cosmetic compositions are extremely resistant to moisture from rain and snow as well as ocean, lake and swimming pool water, yet they are easily removed with soap and water.

The present invention further relates to a waterproof cosmetic composition useful as a mascara which comprises a dimethicone-silica copolymer, volatile organic solvent, colorant, and wax in a water-in-oil emulsion.

DETAILED DESCRIPTION OF THE INVENTION

The present invention encompasses a waterproof cosmetic composition which comprises a dimethicone-silica copolymer in an emulsion system, which composition is, in particular, useful as a waterproof mascara. Generally, the cosmetic compositions of the present invention also comprise a cosmetically acceptable volatile organic solvent or a combination of volatile organic solvents in addition to the dimethicone-silica copolymer. These solvents are volatile in that they evaporate quickly upon application of the mascara to eyelash or eyebrow hair. Although not being limited by theory, it is believed that when the solvent evaporates the mascara composition "drys" and forms a cross-linked dimethicone/silica copolymer film. It is this film, itself and in combination with other components of the cosmetic composition, that provides the unique wear and removal characteristics of the cosmetic compositions of the present invention.

For example, the cosmetic compositions of the present invention are clearly water-resistant to moisture, including treated swimming pool water, fresh water and ocean water. The cosmetic composition is smudge resistant and does not flake. Yet, the composition is easily removed with the use of simply soapy water. Of course, the compositions can also be removed by cosmetic cleansers well known to those skilled in the art such as cleansing oils or emulsions.

The general ingredients for the cosmetic compositions of the present invention are the dimethicone-silica copolymer, water, and a cosmetically acceptable organic material. These ingredients when combined are capable of forming an emulsion with or without the use of cosmetically acceptable emulsifiers. In other words, the general ingredients are a dimethicone-silica copolymer in an emulsion system. The preferred ingredients for the waterproof cosmetic composition of the present invention, which is useful as a mascara, are: (a) a cosmetically acceptable volatile organic solvent or solvents; (b) water; (c) dimethicone-silica copolymer; (d) a cosmetically acceptable colorant or pigment; and (e) cosmetically acceptable wax. Optionally, additional ingredients known to those skilled in the art, such as cosmetically acceptable fillers, film-forming agents, preservatives, and emulsifiers can be used if desired. Such commonly used ingredients can be found in the CTFA International Cosmetic Ingredient Dictionary, 4th Edition, published by The Cosmetic, Toiletry and Fragrance Association, Inc., Washington, D.C., 1991, the disclosure of which is hereby incorporated by reference. Most preferably, the ingredients for the waterproof cosmetic compositions of the present invention are a cosmetically acceptable volatile organic solvent or solvents; water; dimethicone-silica copolymer; a cosmetically acceptable colorant or pigment; cosmetically acceptable wax and cosmetically acceptable emulsifiers.

The preferred ingredients are generally used within the following ranges, in weight percent, volatile organic solvent from about 15 to about 85%, preferably about 25 to 65% and most preferably about 30 to 40%; water from about 2 to about 25%, preferably about 5 to 20% and most preferably about 10 to 15%; dimethicone-silica copolymer, as the commercially available emulsion, from about 1 to about 25%, preferably about 5 to 10%; colorant from about 1 to about 20%, preferably about 8%; cosmetic waxes from about 5 to about 75%, about 10 to about 50%; and preferably about 15 to 25%. Optional ingredients can be used within the following ranges, in weight percent, cosmetic fillers from about 1 to about 10%; cosmetic preservatives from about 0.01 to about 2%; and cosmetic emulsifiers from about 0.01 to about 15%.

The dimethicone-silica copolymer which is used in the cosmetic compositions of the present invention can be obtained from Dow Corning as an emulsion (Dow Corning ® 7-4116 Cosmetic emulsion). The water used with the present cosmetic composition is preferably distilled or deionized water; however, tap water is suitable. The volatile organic solvents within the scope of the present invention are those organic solvents which are cosmetically acceptable and are compatible with the dimethicone-silica copolymer and which also quickly evaporate upon application of the composition to the eyelash, etc. Volatile organic solvents within the scope of the present invention include, but are not limited to petroleum distillate, isoparaffin, cyclomethicone, isododecane, isohexadecane and the like. It will be appreciated by those skilled in the art that any combination of such cosmetically acceptable solvents described above, as well as those known to persons skilled in the art, can also be used.

Since the cosmetic compositions of the present invention are most useful as mascaras, these can also contain colorants or pigments for imparting color to the eyelashes or eyebrows to which the composition is applied; however, colorants or pigments are not necessary. Cosmetically acceptable colorants within the scope of the present invention include, but are not limited to, iron oxides (black, red, and yellow); ultramarine blue, ferric ammonium ferrocyanide, carmine, manganese violet, ultramarine pink, ultramarine violet, chromium hydroxide green, chromium oxide greens, titanium dioxide and the like. It should also be noted that any combination of colorants can be used within the present compositions.

The inventors have found that cosmetically acceptable waxes can be used in the cosmetic compositions of the present invention while retaining the unique wear and removal characteristics. The cosmetically acceptable waxes within the scope of the present invention include, but are not limited to, carnauba, candelilla wax, ozokerite, microcrystalline wax, beeswax, synthetic wax, paraffin and the like. Any combinations of these or other cosmetically acceptable waxes known to those skilled in the art is also acceptable. Again, any optional ingredients known to those skilled in the art may also be used without deviating from the spirit or scope of the present invention. Examples of optional ingredients are cosmetic fillers including, but not limited to, talc, nylon, mica, sericite, polyethylene, silica, polymethylmethacrylate, bismuth oxychloride, kaolin, PTFE; cosmetic preservatives including, but not limited to, methylparaben, propylparaben, butylparaben, ethylparaben, potassium sorbate, trisodium EDTA; phenoxyethanol, benzyl alcohol, chloroxylenol, imidazolidinyl urea, citric acid; and cosmetic emulsifiers including, but not limited to, ethoxylated alcohols, ethoxylated fatty acids, fatty esters, ethoxylated fatty esters, glycerol esters, glycol esters, lanolin based derivatives, soaps, sucrose and glucose esters and derivatives. Additionally, film-forming agents which augment the film-forming properties of the dimethicone-silica copolymer can also be used. These include, but are not limited to, PVP/Hexadecene, PVP/Eicosene and tricontanyl PVP. The ingredients described above can be found in the CTFA International Cosmetic Ingredient Dictionary, 4th Edition 1991.

Any cosmetically acceptable emulsion system can be employed in the present invention. Either water-in-oil or oil-in-water systems can be used; however, water-in-oil is preferred. Although the use of emulsifiers is not necessary, emulsifiers are preferred for use in the present compositions. Preferably, the emulsion is a blend of a soap system, and selected non-ionic emulsifiers. The emulsion must be capable of solubilizing (must be compatible) with the dimethicone-silica copolymer.

A preferred cosmetic composition of the present invention is a waterproof cosmetic composition useful as a mascara, which comprises a dimethicone-silica copolymer, cosmetically acceptable wax and a colorant in a water-in-oil emulsion. A further preferred embodiment of the present invention is a waterproof cosmetic composition useful as a mascara, which comprises a dimethicone-silica copolymer, volatile organic solvent, cosmetically acceptable wax and a colorant in a water-in-oil emulsion.

The present invention also encompasses methods of using the above-described cosmetic compositions to both beautify and protect eyelashes. One method is protecting and/or beautifying eyelashes or eyebrows with a waterproof mascara which comprises applying an effective amount of a cosmetic composition described above to the eyelashes or eyebrows. In addition, the present invention includes a method of coating eyelashes or eyebrows with a waterproof dimethicone-silica copolymer, which is easily removed with soapy water, which comprises applying an effective amount of a cosmetic composition described above to the eyelashes or eyebrows. As mentioned above, upon evaporation of the volatile organic solvent, the dimethicone-silica copolymer crosslinks to form a dimethicone-silica copolymer film with unique wear and removal characteristics. It will be appreciated that an effective amount means an amount sufficient to cover the surface area of the eyelashes or eyebrows. This amount will vary with the user according to the size and amount of eyelashes or eyebrows and amount of mascara desired.

The method of the present invention further comprises removing the composition with a soap and water solution. In addition, as mentioned above, the cosmetic compositions of the present invention can be removed with the use of cosmetic cleaners.

The following examples are given to illustrate the scope of the present invention. Because these examples are given for illustrative purposes only, the invention should not be inferred to be limited to these examples.

EXAMPLES

An example of a preferred cosmetic composition according to the present invention is represented by the following formulation:

EXAMPLE 1
Preparation of a Waterproof Mascara - Black

| INGREDIENT | APPROXIMATE WEIGHT PERCENT |
| --- | --- |
| Petroleum Distillate | 32.9 |
| Water | 12.5 |
| Dimethicone-Silica Copolymer with Cyclomethicone in an Ammonium Lauryl Sulfate emulsion from Dow Cornings ® | 10.0 |
| Iron Oxides | 8.0 |
| Carnauba | 6.8 |
| Candelilla Wax | 6.8 |
| C8-9 Isoparaffin | 5.0 |
| Beeswax | 3.4 |
| Lanolin Acid | 3.0 |
| PEG-20 Sorbitan Beeswax | 2.75 |
| Ozokerite | 2.55 |
| Nylon-12 | 2.0 |
| PVP/Eicosene Copolymer | 2.0 |
| Phenoxyethanol | 1.0 |
| Parabens | 0.3 |
| Ammonium Hydroxide | 0.54 |
| Potassium Sorbate | 0.3 |
| Trisodium EDTA | 0.05 |

The cosmetic compositions of the present invention can be prepared by blending together the essential and optional ingredients described above. A black waterproof mascara was prepared according to the following procedure. In a suitable support mixing vessel equipped with means for providing agitation (i.e., a support steam-jacketed kettle with a propeller mixer) combine waxes (carnauba wax, candelilla wax, ozokerite, beeswax-white, lanolin acid, PEG-20 sorbitan beeswax, PVP/Eicosene, and parabens (butylparaben and propylparaben) and petroleum distillate- Heat the materials to about 85° C. with agitation. Mix until the solids are dissolved and the phase is uniform. Transfer the mixture to a primary steam-jacketed kettle with a propeller mixer and a counter-rotating side-wiping agitator through a mesh nylon bag (100-150 mesh). With mixing and heating continued (85° C.) slowly add nylon-12 and colorant. Mix until completely uniform and dispersed (about 5 to 10 minutes). Discontinue mixing with lightning mixer agitation and begin mixing with a homogenizing mixer while maintaining 85° C. temperature. Combine water, trisodium EDTA, potassium sorbate and methyl paraben USP in the support kettle. Heat to 85° C. with mixing and continue mixing until all solids are dissolved and the phase is clear. When the mixture is at 85° C., just prior to emulsification, add ammonium hydroxide (28% ammonia) to the mixture in the support kettle while mixing. Add the contents of the support kettle (aqueous phase) (at 85° C.) to the primary kettle (oil phase) (at 85° C.) with the homogenizing mixer agitation. When addition is complete maintain 83°-85° C. and mix for 15 minutes. Continuing mixing and begin to air cool to 65° C. At 65° C. stop cooling and add Dow Corning ® 7-4116 cosmetic emulsion, phenoxyethanol, C8-9 isoparaffin and petroleum distillate, one at a time while mixing, and mix well between each addition. At completion of last addition, remove the homogenizing mixer and resume cooling to 25° C. with side wiping agitation.

EXAMPLE 2
Preparation of a Waterproof Mascara - Colorless

| INGREDIENT | APPROXIMATE WEIGHT PERCENT |
| --- | --- |
| Petroleum Distillate | 39.99 |
| Cyclomethicone | 10.25 |
| Water | 20.00 |
| Ammonium Lauryl Sulfate | 0.01 |
| Dimethicone-Silica Copolymer (Dow Corning ® 7-4116) | 6.00 |
| Carnauba | 7.00 |
| Candelilla Wax | 7.00 |
| Microcrystalline Wax | 5.00 |
| Lanolin Acid | 3.00 |
| Ammonium Hydroxide | 0.75 |
| Benzyl Alcohol | 0.50 |
| Parabens | 0.50 |

A colorless mascara composition, comprising the ingredients in the above table, is prepared in accordance with the procedure of Example 1.

EXAMPLE 3
Preparation of Waterproof Mascara
Without Volatile Organic Solvents

| INGREDIENT | APPROXIMATE WEIGHT PERCENT |
| --- | --- |
| Water | 55.44 |
| Dimethicone-Silica Copolymer (Dow Corning ® 7-4116) | 7.00 |
| Ammonium Lauryl Sulfate | 0.01 |
| Iron Oxides | 8.00 |
| Nylon-12 | 2.00 |

EXAMPLE 3
Preparation of Waterproof Mascara
Without Volatile Organic Solvents

| INGREDIENT | APPROXIMATE WEIGHT PERCENT |
|---|---|
| Carnauba | 7.50 |
| Candelilla Wax | 7.50 |
| Polybutene | 5.00 |
| Glyceryl Stearate | 3.00 |
| Stearic Acid | 3.00 |
| Morpholine | 0.75 |
| Imidazolidinyl Urea | 0.30 |
| Parabens | 0.50 |

A colored mascara composition, comprising the ingredients in the above table, is prepared in accordance with the procedure of Example 1.

It may be apparent to those skilled in the art that modifications and variations of the present invention are possible in light of the above disclosure. It is understood that such modifications are within the spirit and scope of the invention, which is limited and defined only by the appended claims.

What is claimed is:

1. A waterproof cosmetic composition useful as a mascara, comprising a dimethicone-silica copolymer, a volatile organic solvent, and at least one cosmetically acceptable wax, in a cosmetic emulsion.

2. A waterproof cosmetic composition of claim 1 wherein said emulsion is water-in-oil or oil-in-water.

3. The waterproof cosmetic composition of claim 1 further comprising a cosmetically acceptable volatile organic solvent and a colorant in a water-in-oil emulsion.

4. The waterproof cosmetic composition of claim 2 or 3 wherein said water-in-oil emulsion is anionic or nonionic.

5. The waterproof cosmetic composition of claim 1 wherein said emulsion system is a soap system.

6. A waterproof cosmetic composition useful as a mascara, which is easily removed with soap and water, comprising:
   (a) from about 5 to about 25 weight % of a dimethicone-silica copolymer;
   (b) from about 5 to about 75 weight % of at least one cosmetically acceptable wax; and
   (c) from about 1 to about 20 weight % of colorant in an emulsion system.

7. A waterproof cosmetic composition useful as a mascara, which is easily removed with soap and water, comprising:
   (a) from about 1 to about 25 weight % of a dimethicone-silica copolymer;
   (b) from about 2 to about 25 weight % of water;
   (c) from about 15 to about 85 weight % of a volatile organic solvent;
   (d) from about 5 to about 75 weight % of at least one cosmetically acceptable wax; and
   (e) from about 1 to about 20 weight % of colorant.

8. The waterproof cosmetic composition of claim 6 or 7 which further comprises cosmetic fillers, cosmetic preservatives, cosmetic film forming agents and cosmetic emulsifiers.

9. The waterproof cosmetic composition of claim 3 or 7 wherein said volatile organic solvent is selected from the group consisting of petroleum distillate, isoparaffin, cyclomethicone, isododecane and isohexadecane.

10. The waterproof cosmetic composition of claim 6 or 7 wherein said cosmetically acceptable wax is selected from the group consisting of carnauba, candelilla wax, ozokerite, beeswax, microcrystalline wax, synthetic wax and paraffin.

11. The waterproof cosmetic composition of claim 3, 6 or 7 wherein said colorant is selected from the group consisting of iron oxides, ultramarine blue, ferric ammonium ferrocyanide, carmine, manganese violet, ultramarine pink, ultramarine violet, chromium hydroxide green, chromium oxide green and titanium dioxide.

12. The waterproof cosmetic composition of claim 8 wherein said emulsifier is selected from the group consisting of ethoxylated alcohols, ethoxylated fatty acids, fatty esters, ethoxylated fatty esters, glycerol esters, lanolin based derivatives, soaps, sucrose esters and derivatives, and glucose esters and derivatives.

13. The waterproof cosmetic composition of claim 7 wherein said dimethicone-silica copolymer is about 10 weight %.

14. The waterproof cosmetic composition of claim 7 wherein said water is about 12.5 weight %.

15. The waterproof cosmetic composition of claim 7 wherein said volatile organic solvent is about 30 to about 40 weight %.

16. The waterproof cosmetic composition of claim 7 wherein said cosmetically acceptable wax is about 15 to about 25 weight %.

17. The waterproof cosmetic composition of claim wherein said colorant is about 8 weight %.

18. A waterproof cosmetic composition useful as a mascara, which comprises petroleum distillate, water, dimethicone-silica copolymer, cyclomethicone, iron oxides, carnauba, candelilla wax, isoparaffin, beeswax, lanolin acid, PEG-20 sorbitan beeswax, ozokerite, nylon-12, PVP/eicosene copolymer, phenoxyethanol, parabens, ammonium hydroxide, potassium sorbate and trisodium EDTA.

19. A method for coating eyelashes with a waterproof dimethicone/silica copolymer film which comprises applying an effective amount of a cosmetic composition of claim 1, 6 or 7.

20. A method for protecting and beautifying eyelashes with a waterproof mascara which comprises applying an effective amount of a cosmetic composition of claim 1, 6 or 7.

21. The method of claim 19 or 20 which further comprises removing said waterproof mascara with a soap and water solution.

* * * * *